United States Patent [19]

Silverstein

[11] 3,943,245
[45] Mar. 9, 1976

[54] PURIFICATION OF PLASMINOGEN
[75] Inventor: Robert M. Silverstein, Homewood, Ill.
[73] Assignee: Armour Pharmaceutical Company, Phoenix, Ariz.
[22] Filed: Feb. 14, 1974
[21] Appl. No.: 440,206

[52] U.S. Cl. .............................. 424/101; 260/112 B
[51] Int. Cl.² ................. A61K 35/14; A61K 35/16; C07G 7/00; C07G 7/026
[58] Field of Search .................. 424/101; 260/112 B

[56] References Cited
UNITED STATES PATENTS
3,234,106   2/1966   Hink, Jr. .............................. 424/101

OTHER PUBLICATIONS
Brockway et al., J. Biol. Chem., 246, pp. 4641–4647 (1971).
Science, 170, pp. 1095–1096 (1970).
Chemical Abstracts, Vol. 80:67938g and 142556m (1974).

Primary Examiner—Donald B. Moyer
Attorney, Agent, or Firm—Richard R. Mybeck

[57] ABSTRACT

The purification of plasminogen from human and non-human mammalian plasma or Cohn Fraction III by modified affinity chromotography using Sepharose-L-lysine with high ionic strength buffer solutions as in ion exchange chromatography is described. A plasminogen is produced in great yield having unexpectedly enhanced activity toward N α-CBZ-L-lysine p-nitrophenyl ester, enhanced fibrinolytic activity and significantly less contamination by unknown colloidal substances.

3 Claims, No Drawings

PURIFICATION OF PLASMINOGEN

The present invention relates to the purification of plasminogen to render it useful for medical purposes and especially pediatric purposes. More particularly, the present invention relates to the discovery of a new and improved method of purification of plasminogen utilizing techniques of modified affinity chromatography to produce a significantly purer and more active plasminogen than has heretofore been available. The method, as will appear, is well suited to both batch and columnar production cycles.

Affinity chromatography with L-lysine covalently attached to Sepharose activated with cyanogen bromide has heretofore been used to purify the plasminogens of several mammalian species. See, for instance, Deutsch et al, "Plasminogen: Purification from human plasma by affinity chromatograph" Science: 170, 1095 (1970); Brockway et al, "The mechanism of the inhibition of plasmin activity by E-aminocaproic acid" J. Biol. Chem., 246, 4641 (1971); and Summaria et al, "Isolation, characterization and comparison of the S-carboxy methyl heavy (A) and light (B) chain derivatives of cat, dog, rabbit and bovine plasmins" J. Biol. Chem., 248, 6522 (1973).

The modified affinity chromatography of the present invention represents an improvement on the conventional methodology by incorporating thereinto an ion exchange principal effected by the selective choice of reagents as will appear hereinafter in detail.

Plasminogen has appeared on the medical horizon as a significant fibrinolytic agent having properties signalling a major breakthrough for the treatment of hyaline membrane disease or respiratory distress syndrome.

Hylamine membrane disease has been the source of great tragedy to families of all walks of life for years.

Clara L. Ambrus, M.D., Ph.D. and Julian Ambrus, M.D., Ph.D., at Roswell Park Memorial Institute, Buffalo, New York, have reported that approximately six hours after birth, the lungs undergo physiological changes and fibrin is deposited in the lung. If the fibrin is left undissolved, the infant will suffocate and expire.

Plasminogen is the precursor of plasmin which dissolves fibrin blood clots. Fibrin, when digested by plasmin, becomes a soluble degradation product and is systemically carried away thereby removing the cloud of suffocation from over the infant's crib.

The threat of hyaline membrane disease looms large after the delivery of a premature infant, infants for diabetic mothers, infants obtained by traumatic delivery procedures, and infants from mothers who experienced bleeding complications during pregnancy.

The threat is dispelled by the administration of a high quality plasminogen, usually parenterally through the umbilical stump in an aqueous vehicle.

The primary motivation resulting in the present invention was the need to provide high quality uncontaminated plasminogen in high yields for use in those life-saving procedures described above.

Accordingly, one of the principal objects of the present invention is to provide a high quality contaminant-free plasminogen for used in medicine, especially pediatric medicine which, when prepared by the method of the invention, is found to be isotonic with blood itself.

Another object of the present invention is to provide a new and useful method for isolating plasminogen from, for example, Fraction III of human plasma (fractionated according to the method of E. J. Cohn), plasma, serum or the euglobulin fraction to produce a superior plasminogen.

Still another object of the present invention is to provide a new and improved method of purifying plasminogen which is well suited to commercial scale and capable of producing plasminogen in quantities to meet need and at a price which will permit the therapeutic benefits to be available to all stations of life.

A still further object of the present invention is to provide a method which is also suited for the purification of plasminogen from mammalian blood of both human and non-human sources in both batch and continous production cycles.

Another object of the present invention is to provide a new and improved method of isolating plasminogen which utilizes non-thrombogenic reagents, is easily reproducible and which provides a product that is readily soluble in aqueous buffer, is free of measurable plasmin, and which is of superior therapeutic quality by virtue of the gentle procedures by which it is isolated.

These and still further objects as shall hereinafter appear are realized by the present invention in a remarkably unexpected fashion as can be readily discerned from a careful reading of the following description of preferred embodiments for the practice thereof.

The effect of ionic strength upon the isolation of human plasminogen by affinity chromatography with Sepharose-L-lysine was found to be an important and surprising utilization of ion exchange chromatography, especially for the purification of human plasminogen from Cohn Fraction III, considered representative of the starting materials embraced herewithin.

In one practice of the present invention, an extract of human Cohn Fraction III in 0.01 M NaCl, 0.01 M potassium phosphate buffer, pH 7.4 was applied to a column of Sepharose-L-lysine. A linear salt gradient to 0.5 M NaCl, 0.01 M potassium phosphate buffer, pH 7.4, eluted two major peaks. The plasminogen was then eluted by adding 0.1 M 6-amino-hexanoic acid to the buffer which was then profiled against plasminogen obtained by the prior art methodology described by Brockway and Castellino in *J. Biol. Chem.*, Vol. 246, 4641 (1971). The remarkably unexpected properties of the plasminogen and methods of the present invention appear hereafter.

The salient features of the present invention comprise the use of modified affinity chromatography to purify plasminogen in which a high ionic strength buffer solution containing a component selected from the group consisting of salts described in step 1 below is employed to create an ion exchange mechanism which results in the separation of a more active plasminogen preparation from a plasminogen-containing starting material; initially treated with a buffer containing EDTA to render that material non-thrombogenic and thereafter engaged with the Sepharose lysine resin and washed with a material having a high salt concentration to elute impurities therefrom. After the ion-exchange chromotography is completed, the plasminogen is freed from the column by an affinity mechanism using 6-amino-hexanoic acid, L-lysine and their known equivalents. It should be noted, however, that while 6-AH is useful to remove plasminogen from the resin, its use should be avoided when the plasminogen is for clinical or diagnostic use because of its antifibrinolytic properties. Of course, if convenient, 6-AH may still be used to elute plasminogen from the resin if it is then completely removed from the plasminogen prior to clinical or diagnostic use. The preferred reagent therefore is L-lysine.

The steps of a preferred practice of the invention are characterized as follows:

1. The starting material is human plasma, non-human mammalian plasma, or Cohn Fraction III prepared from human plasma. This material is suspended in a buffer solution of high ionic strength which contains EDTA (ethylenediamine tetraacetic acid) and the suspension is subjected to intense vibration in a mixer.

The salts used in preparing the suspension include sodium, potassium and lithium, chloride, fluoride, bromide and phosphate, and (Tris) buffer and barbital buffer, in concentrations ranging from 0.2 M (molar) to 1.0 M, and pH ranges of from 5.5. – 8.5. The EDTA acts as an anticoagulant and prevents fibrin formation. This step results in a more complete suspension of the starting material in less time than has been possible with previous methods. An additional advantage gained by this step is the prevention of thrombin activation.

2. In this step the suspension is centrifuged and the supernatant is applied to a column of the affinity resin (Sepharose-L-lysine) in a downward direction. The column is washed downwardly with 0.5 M NaCl, 0.01 M $KPO_4$ buffer (pH 7.4), and thereafter was in an upwardly direction with 0.15 M NaCl, 0.01 M $KPO_4$ buffer (pH 7.4). Use of high ionic strength buffer solutions in this step results in fewer impurities binding to the affinity column and the washing can be done in less time.

3. In this step the plasminogen is eluted from the column by causing a buffer solution containing L-lysine (0.1 M L-lysine, 0.1 M NaCl, 0.01 M $KPO_4$ — pH 7.4) to flow upwards through the affinity column. The advantages gained in this step are that no antifibrinolytic agent (6-aminohexanoic acid or epsilon aminocaproic acid) is used, as is found in existing methods for the extraction of plasminogen, and a purer, more concentrated and active plasminogen product is obtained.

4. Plasmin activity is measured by a procedure in which plasminogen is activated to plasmin with streptokinase and thereafter assayed with carbobenzoxy-L-lysine -p-nitrophenyl ester as the substrate. The degree of hydrolysis is measured by means of a spectrophotometer.

As a further aid in the understanding of the present invention, and not by way of limitation, the following examples are presented.

EXAMPLE I

The starting material for these examples was Cohn Fraction III obtained from Armour Pharmaceutical Company, Kankakee, Illinois (lot AP 2091). Reagent grade salts and pyrogen-free distilled water were also used throughout. Sepharose-L-lysine was prepared according to the procedure outlined by Brockway et al, ibid, using 150 ml Sepharose 4-B, 20 g cyanogen bromide and 6 g of L-lysine H Cl. The various buffers employed in this and succeeding examples are defined in Table I below.

Fraction III (2.7 g) was suspended in 100 ml of selected buffers using a Vibro-mixer, model E-1 (Chemap, Inc.,) for about 30 minutes at room temperature. The suspension was centrifuged at 12,100 g for 10 minutes at 4° and the supernatant was applied to a column of Sepharose-L-lysine (1.5 × 15 cm) equilibrated by one of the buffers hereafter described. No activity was recovered in the pellet or in the eluate unbound by the column. The columns were eluted using various buffer systems described in the specific examples.

Plasmin activity was measured by activating the zymogen to plasmin with streptokinase and assaying with $N^\alpha$-CBZ-L-lysine p-nitrophenyl ester (CLN) as the substrate as described in my aforesaid copending application. Polyacrylamide gel electrophoresis was performed in Gradipore slabs (4–26% acrylamide) as described in Maurer. *Disc Electrophoresis and Related Techniques of Polyacrylamide Gel Electrophoresis*, Berlin and New York, Walter der Gruyter (1971) p. 60.

The buffers employed in this work are herein identified by the following code:

TABLE I

| Code | BUFFERS System Composition |
|---|---|
| A | 0.01 M potassium phosphate buffer, pH 7.4 |
| A (EDTA) | Buffer A with 1 mM EDTA |
| A (0.1) | Buffer A with 0.1 M NaCl |
| A (0.5) | Buffer A with 0.5 M NaCl |
| A (0.01, EDTA) | Buffer A with 0.01 M NaCl and 1 mM EDTA |
| A (0.5, EDTA) | Buffer A with 0.5 M NaCl and 1 mM EDTA |
| B | 0.3 M potassium phosphate buffer, pH 7.4 |
| B (EDTA) | Buffer B with 1 mM EDTA |
| C | Buffer A (0.1) with 0.1 M 6-AH |
| D | 0.2 M 6-AH, 0.1 M potassium phosphate buffer, pH 7.4 |
| E | 0.1 N acetic acid |

EXAMPLE II

The chromatography of the Fraction III extracted with buffer B (EDTA) on Sepharose-L-lysine equilibrated with buffer B was determined according to the published procedures. See:Brockway, W. J. and Castellino, F. J. The mechanism of the inhibition of plasmin activity by E-aminocaproic acid. *J. Biol. Chem.*, 246, 4641 (1971). A large amount of protein was washed through the column. Buffer B was then applied to the column and no more protein was eluted. The column was thereafter washed with buffer D to elute a single peak containing plasminogen. This material had a specific activity of 3.9 u/$A_{280}$ ml. This material was colloidal. The column was then washed with buffer E which eluted much of the colloidal material.

EXAMPLE III

Fraction III was prepared in buffer A (0.01, EDTA) and was applied to a column prepared as in Example I. Much protein was eluted at the beginning of the experiment. Additional protein was eluted by buffer A. A salt gradient of buffer A and buffer A (0.5) was begun. This eluted one complex protein peak at about 450 mls followed by a second sharp peak at 600 mls. A salt gradient is a means by which the salt content of the eluting buffer is carefully and slowly increased. At the end of the gradient, additional protein was obtained upon washing with A (0.5). The plasminogen was then eluted by addition of 6-AH to buffer A (0.1). The plasminogen had a specific activity of 4.8 u/$A_{280}$ ml and was clear. Further protein was eluted by washing the column with buffer E.

From the foregoing, it was concluded that ion exchange chromatography had occurred because different proteins were eluted when the salt concentration in the buffer was increased. It was also shown by the change in pH. On the other hand, affinity chromatography also occurred because the plasminogen could only be freed from the column with a specific inhibitor. Increasing salt concentration could not free the plasminogen from the column.

The results obtained in Examples II and III led to the development of the new and improved method of isolating plasminogen that is the subject of this disclosure.

EXAMPLE IV

Plasminogen was extracted from Fraction III using buffer A (0.5, EDTA). The column was also equilibrated in the same buffer to avoid the ion exchange chromatography observed in Example III when the salt gradient was used. When the extract was applied to the column in this buffer, much protein came through the column. Further washing with buffer A (0.1) did not elute much additional protein. The plasminogen was then eluted with buffer C to provide a material having a specific activity of 4.7 $u/A_{280}$ ml and which was completely clear.

EXAMPLE V

The procedure of Examples I and II was repeated by suspending portions of Fraction III respectively in buffers A (EDTA), A (0.01, EDTA), A (0.5, EDTA) and B (EDTA). The several suspensions were then each centrifuged at 12,100 g for 10 minutes at 4°C and the supernatants obtained therefrom were applied to a column of Sepharose-L-lipine (1.5 × 15 cm). The columns were selectively equilibrated in buffers A, A (0.1), A (0.5) and B.

In every case, no activity was recovered in the pellet or in the eluate unbound in the column.

The columns were then eluted using the buffer systems described and the plasminogen obtained therefrom was found to be in high yield with high activity and substantially no contamination.

EXAMPLE VI

The effect of ionic strength on the elution of plasminogen by 6-AH or lysine was found to be significant. The procedures of Examples I and II were repeated but the plasminogen was eluted with 0.1 M 6-AH in 0.01 M potassium phosphate buffer with no sodium chloride. A large volume of zymogen was eluted from the column from which it was concluded that the desorption of plasminogen is ionic strength dependent. It was also determined that the efficiency of elution was dependent on the concentration of 6-AH. When plasminogen was eluted with 0.02 M 6-AH in buffer A (0.1), the product was somewhat dilute. From this, we can conclude that an eluting buffer such as C is satisfactory though not necessarily optimal. Other considerations will, of course, control the selection of this buffer as was previously elucidated.

From the foregoing examples, it is apparent that ion exchange and affinity chromatography both occur when a Cohn Fraction III extract is chromatographed on Sepharose-L-lysine. The ion exchange effect is clearly demonstrated in Example III where two peaks were eluted by increasing ionic strength. It is also shown that the desorption of plasminogen from Sepharose-L-lysine is due to a specific interaction with L-lysine or 6-AH.

While it was observed that the addition of 0.1 M 6-AH to 0.1 M NaCl, 0.01 M potassium phosphate buffer, pH 7.4, had a negligible effect on the ionic strength as measured by conductivity, elution is less efficient with concentrations less than 0.1 M NaCl and 0.1 M 6-AH. Thus, the elution of plasminogen does not appear to occur by a gross change in ionic strength but rather by the highly specific and ionic-strength-dependent interaction between the bound plasminogen and the unbound 6-AH.

From the foregoing, it becomes readily apparent that a new and useful method of purifying plasminogen has been herein described and illustrated which fulfills all of the aforesaid objectives in a remarkably unexpected fashion. It is, of course, understood that such modifications, alterations and adaptations as may readily occur to the artisan confronted with this disclosure are intended within the spirit of this invention, limited only by the scope of the claims affixed hereto.

What is claimed is:

1. In the affinity chromatography method of isolating and purifying plasminogen from mammalian and human plasmas and Cohn III fractions comprising the steps of extracting the plasminogen, supplying the plasminogen-bearing extract to a L-lysine sepharose column, washing said column to elute impurities and then eluting the plasminogen, the improvement to the method comprising using a solution comprising about 0.5 molar sodium chloride in the step of washing the column.

2. The method of claim 1 wherein the wash solution has a pH of about 7.4.

3. The method of claim 1 wherein the wash solution contains 0.5 M NaCl and 0.01 M $KPO_4$ at pH 7.4.

* * * * *